US00PP36067P2

(12) United States Plant Patent
Hermans

(10) Patent No.: US PP36,067 P2
(45) Date of Patent: Aug. 13, 2024

(54) ***BUXUS* PLANT NAMED 'HER2008114'**

(50) Latin Name: ***Buxus henryi* X *sempervirens***
Varietal Denomination: HER2008114

(71) Applicant: Herplant BVBA, Beerse (BE)

(72) Inventor: Didier Hermans, Beerse (BE)

(73) Assignee: HERPLANT BVBA, Beerse (BE)

( * ) Notice: Subject to any disclaimer, the term of this patent is extended or adjusted under 35 U.S.C. 154(b) by 0 days.

(21) Appl. No.: 18/529,284

(22) Filed: Dec. 5, 2023

(51) Int. Cl.
*A01H 6/00* (2018.01)
*A01H 5/12* (2018.01)

(52) U.S. Cl.
USPC ..... Plt./226

(58) Field of Classification Search
USPC ..... Plt./226
CPC ..... A01H 6/00; A01H 5/00
See application file for complete search history.

*Primary Examiner* — Keith O. Robinson
(74) *Attorney, Agent, or Firm* — Penny J. Aguirre

(57) ABSTRACT

A new cultivar of *Buxus* plant named 'HER2008114' that is characterized by its large leaves (average of 4 cm in length), its leaves that stay green year round (even when planted close together) without browning, its upright growth habit, and its suitability for hedges and cloud pruning.

3 Drawing Sheets

Botanical classification: *Buxus henryi* X *sempervirens*.
Variety denomination: 'HER2008114'.

CROSS REFERENCE TO A RELATED APPLICATION

This application is related to a European plant breeders' rights application filed on Mar. 8, 2022, application No. 2022/0629. The Applicant received the information for the Plant breeders' rights application directly from the Inventor.

BACKGROUND OF THE INVENTION

The present invention relates to a new and distinct cultivar of *Buxus* of hybrid origin and will be referred to hereafter by its cultivar name, 'HER2008114'. 'HER2008114' is a new cultivar of boxwood grown for use as an ornamental landscape plant with particular suitability for hedges and cloud pruning.

The new cultivar was developed from an ongoing breeding program conducted under the direction of the Inventor at his nursery in Beerse, Belgium. 'HER2008114' arose from a cross made in 2008 between an unnamed and unpatented proprietary plant of *Buxus henryi* as the female parent and an unnamed and unpatented proprietary plant of *Buxus sempervirens* as the male parent. The seeds from various crosses were pooled and the exact parentage is unknown. The Inventor selected the new cultivar as a single unique plant from amongst the seedlings of the above cross in 2018.

Asexual propagation of the new cultivar was first accomplished under the direction of the Inventor by stem cuttings in 2018 in Beerse, Belgium. Asexual propagation of the new cultivar by stem cuttings has determined that the characteristics are stable and are reproduced true to type in successive generations.

SUMMARY OF THE INVENTION

The following traits have been repeatedly observed and represent the characteristics of the new cultivar. These attributes in combination distinguish 'HER2008114' as a unique cultivar of *Buxus*.

1. 'HER2008114' exhibits large leaves (average of 4 cm in length).
2. 'HER2008114' exhibits leaves that stay green year round even when planted close together without browning.
3. 'HER2008114' exhibits an upright growth habit.
4. 'HER2008114' exhibits suitability for hedges and cloud pruning.

The female parent plant of 'HER2008114' differs from 'HER2008114' in having arching branches and leaves that are longer. The male parent plant of 'HER2008114' differs from 'HER2008114' in having leaves that are smaller in size. 'HER2008114' can be most closely compared to *Buxus sempervirens* cultivar 'Rotundifolia' (not patented) and *Buxus sinica* cultivar 'Justin Brouwers' (not patented) 'Rotundifolia' differs from 'HER2008114' in having leaves that are shorter and wider in size and a less bushy and more rounded plant habit. 'Justin Brouwers' differs from 'HER2008114' in having much smaller leaves.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include website listings by Planttipp, Plantago, Hortweek, Vakbeurs GrootGroenPlus, Sierteelt En Groen, AVBS, and Gabot.

BRIEF DESCRIPTION OF THE DRAWINGS

The accompanying color photographs illustrate the overall appearance and distinct characteristics of the new *Buxus*.

The photographs were taken of a plant 6 years in age as grown outdoors in 28-cm container in Beerse, Belgium.

Figure 1:
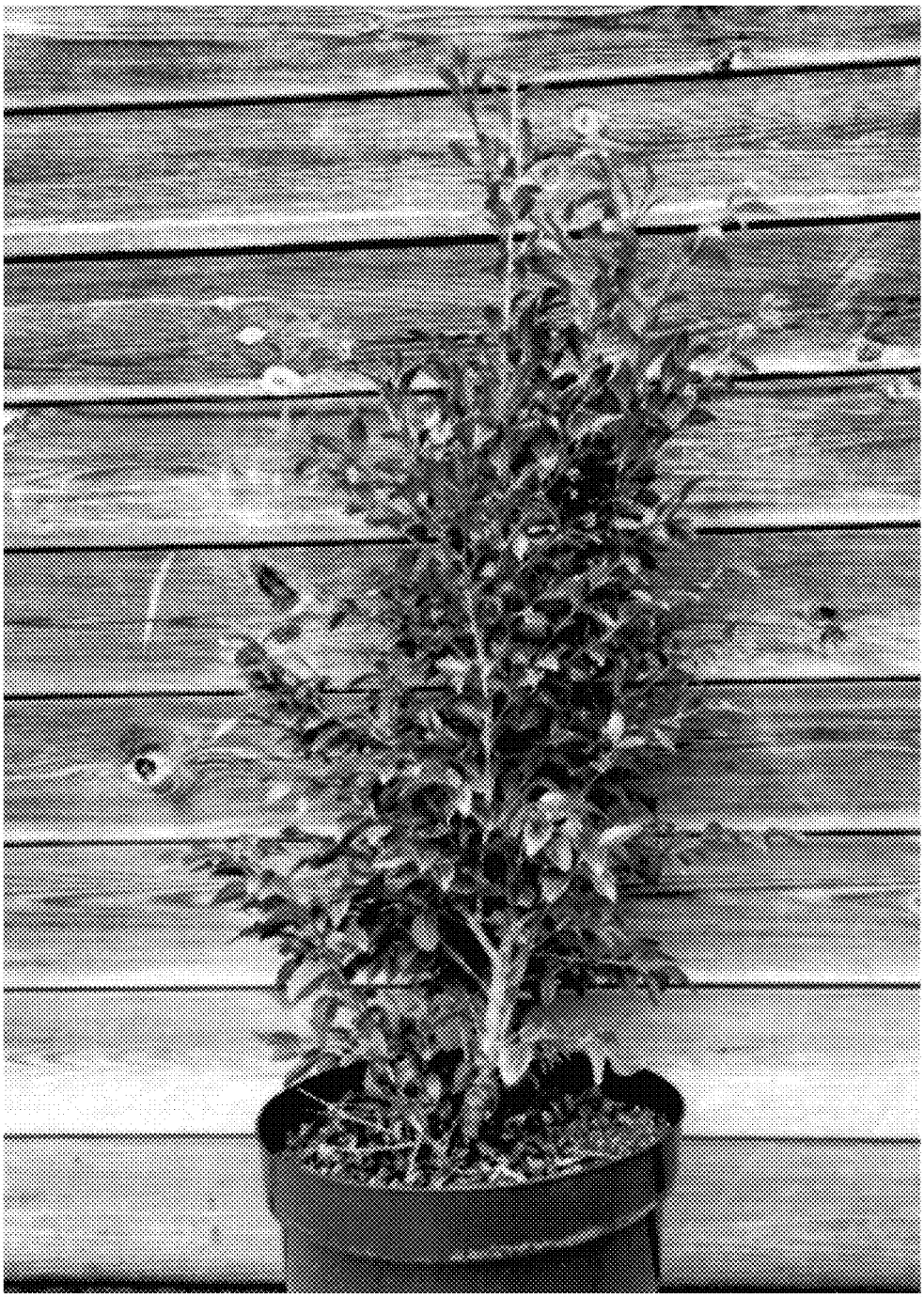

The photograph in FIG. 1 provides a side view of the plant habit of 'HER2008114'.

Figure 2:
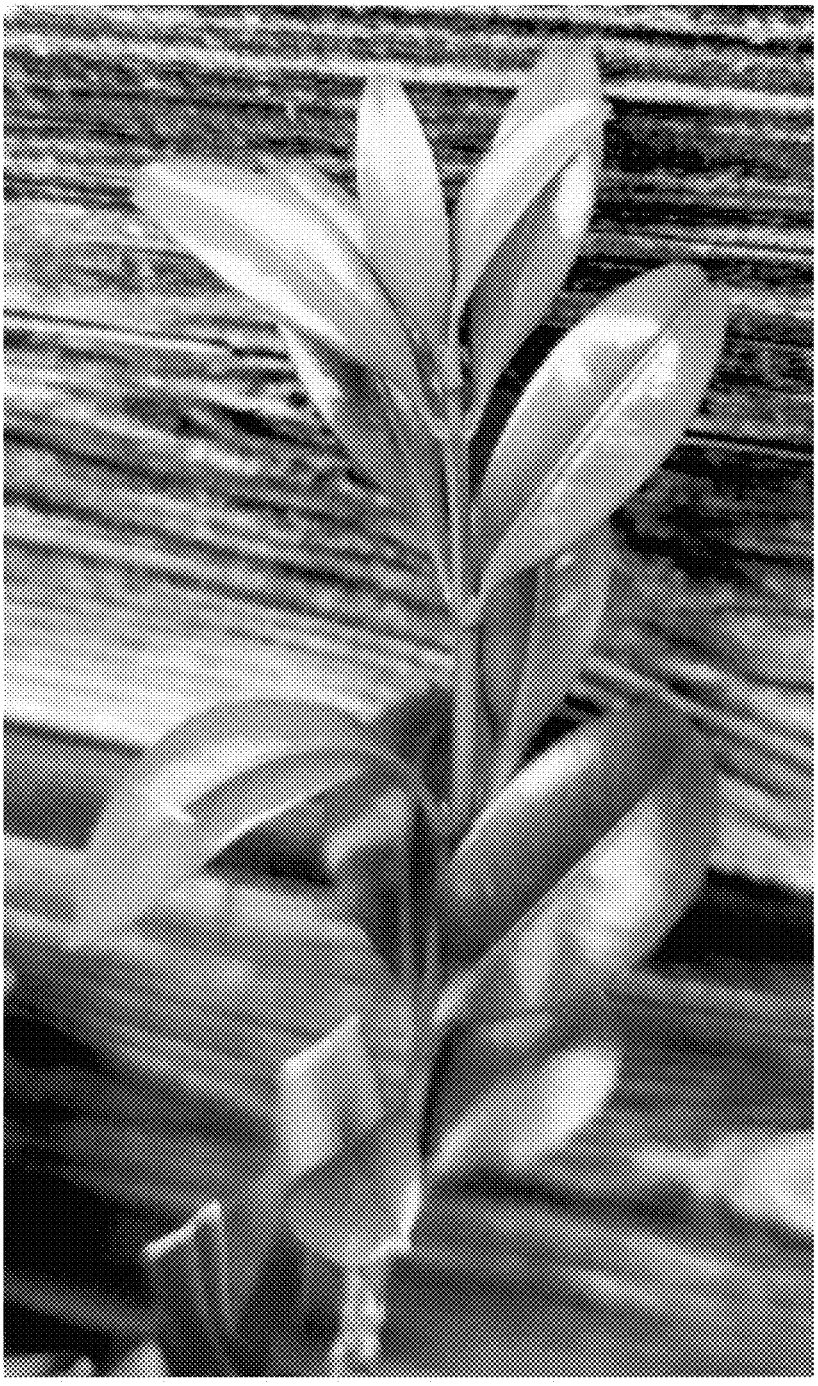

The photograph in FIG. 2 provides a close-up view of the young foliage of 'HER2008114'.

Figure 3:
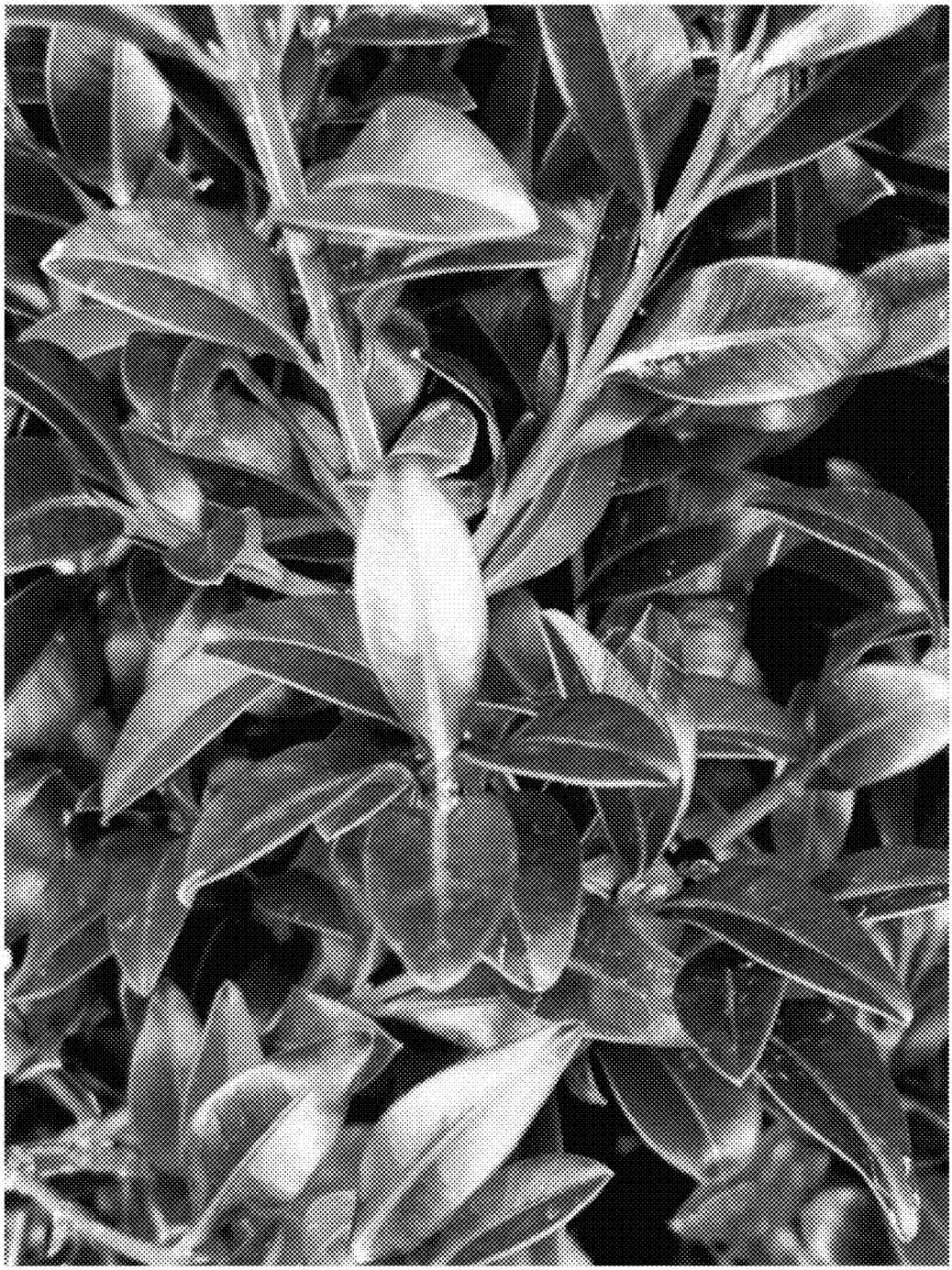

The photograph in FIG. 3 provides a close-up view of the mature foliage of 'HER2008114'.

The colors in the photographs are as close as possible with the photographic and printing technology utilized and the color values cited in the detailed botanical description accurately describe the colors of the new *Buxus*.

DETAILED BOTANICAL DESCRIPTION

The following is a description of 6-year-old plants as grown outdoors in 28-cm containers in Beerse, Belgium. The phenotype of the new cultivar may vary with variations in environmental, climatic, and cultural conditions, as it has not been tested under all possible environmental conditions. The color determination is in accordance with the 2015 Colour Chart of The Royal Horticultural Society, London, England, except where general color terms of ordinary dictionary significance are used.

General description:

*Plant type.*—Evergreen shrub.

*Plant habit.*—Upright, dense.

*Height and spread.*—Average of 78 cm in height, 43 cm in width as a 4-year-old plant grown in the landscape.

*Hardiness.*—At least in U.S.D.A. Zones 5 to 8.

*Diseases and pests.*—No resistance or susceptibility has been observed to diseases or pests.

*Root description.*—Fibrous, 161A in color.

*Propagation.*—Stem cuttings.

*Root development.*—A rooted cutting takes 1.5 years to fully root in a P10.5 container.

*Growth rate.*—Moderate to high.

Branch description:

*Branch shape.*—Rounded.

*Branch color.*—Young stems; 144B, mature stems; 144A, bark and older stems; 161C.

*Branch aspect.*—Average of 80° from vertical.

*Branch size.*—(Averages); main stem; 7 cm in length, 1.9 cm in diameter, secondary stems; 27 cm in length, 8 mm in diameter, lateral stems; 13 cm in length, 3 mm in diameter.

*Branch strength.*—Strong.

*Branch surface.*—Young and mature; glabrous, slightly glossy, woody stems; rugose, matte.

*Branch number.*—An average of 1 primary branch, 2 secondary stems, and 20 lateral branches.

*Branching habit.*—Freely branching.

*Internode length.*—Average of 1.4 cm.

Foliage description:

*Leaf shape.*—Young; lanceolate, mature; ovate.

*Leaf division.*—Simple.

*Leaf arrangement.*—Opposite.

*Leaf base.*—Attenuate.

*Leaf aspect.*—Between 50° and 60° to horizontal.

*Leaf apex.*—Young; acute, mature; slightly emarginate.

*Leaf fragrance.*—Light fresh fragrance.

*Leaf venation.*—Pinnate, young upper surface (only mid-rib is visible) 153B, young lower surface 151A, mature upper surface (only mid-rib is visible) 137B, mature lower surface 144B to 144C.

*Leaf margins.*—Entire.

*Leaf attachment.*—Petiolate.

*Leaf surface.*—Both surfaces smooth, glabrous, glossy and non-rugose.

*Leaf size.*—Average of 4 cm in length and 1.8 cm in width.

*Leaf quantity.*—Average of 14 (7 pairs) on a branch 20 cm in length.

*Leaf color.*—Young upper surface; 153A, young lower surface 151A, mature upper surface; NN137A, mature lower surface 144A.

*Petioles.*—Average of 2 mm in length, 1 mm in width, surface smooth, slightly glossy, strong, young upper and lower surface color 153B, mature upper and lower surface color 144B.

Inflorescence description: No flowers have been observed to date.

It is claimed:

1. A new and distinct cultivar of *Buxus* plant named 'HER2008114' as herein illustrated and described.

* * * * *